United States Patent

Nosu et al.

[11] Patent Number: 5,750,609
[45] Date of Patent: May 12, 1998

[54] ULTRAVIOLET PROTECTIVE AGENT

[75] Inventors: Tsutomu Nosu; Wataru Hiraishi, both of Takamatsu; Yoshiharu Sawa, Sakaide, all of Japan

[73] Assignee: Kyowa Chemical Industry Co., Ltd., Takamatsu, Japan

[21] Appl. No.: 630,324

[22] Filed: Apr. 10, 1996

[51] Int. Cl.$^6$ .............. C08K 3/22; C01G 49/00; C01G 51/00

[52] U.S. Cl. .............. 524/413; 423/594; 423/600; 523/102; 523/122; 524/434; 524/435

[58] Field of Search .............. 524/413, 434, 524/435; 523/102, 122; 423/594, 600

[56] References Cited

U.S. PATENT DOCUMENTS

| | | | |
|---|---|---|---|
| 2,474,215 | 6/1949 | Kearby | 423/600 |
| 2,579,978 | 12/1951 | Snock et al. | 423/600 |
| 3,413,083 | 11/1968 | Daendiker | 423/600 |
| 3,849,545 | 11/1974 | Miklas | 423/594 |
| 3,864,302 | 2/1975 | Foley | 524/606 |
| 4,333,846 | 6/1982 | Lee et al. | 423/600 |
| 4,486,401 | 12/1984 | Arons et al. | 423/594 |
| 4,699,743 | 10/1987 | Nakamura et al. | 424/413 |
| 5,141,980 | 8/1992 | Ranceze et al. | |
| 5,264,284 | 11/1993 | Miyata | 524/436 |
| 5,401,442 | 3/1995 | Miyata | 524/436 |
| 5,422,092 | 6/1995 | Miyata | 423/594 |
| 5,466,740 | 11/1995 | Miyata | 524/436 |
| 5,527,519 | 6/1996 | Miksits et al. | |
| 5,583,172 | 12/1996 | Imahashi et al. | 524/436 |

FOREIGN PATENT DOCUMENTS

| | | | |
|---|---|---|---|
| 0603527 | 6/1994 | European Pat. Off. | |
| 225597 | 7/1985 | Germany | 423/600 |
| 3537624 | 4/1987 | Germany | |
| 46-2280 | 1/1971 | Japan | |
| 47-32198 | 8/1972 | Japan | |
| 48-29477 | 9/1973 | Japan | |
| 48-70719 | 9/1973 | Japan | |
| 51-20997 | 6/1976 | Japan | |
| 51-29129 | 8/1976 | Japan | |
| 51-37640 | 10/1976 | Japan | |
| 55-25133 | 7/1980 | Japan | |
| 56-05330 | 1/1981 | Japan | 423/594 |
| 62-275025 | 11/1987 | Japan | |
| 64-72924 | 3/1989 | Japan | 423/594 |
| 2-14829 | 1/1990 | Japan | |
| 2-286744 | 11/1990 | Japan | |
| 4-325494 | 11/1992 | Japan | |
| 4-325495 | 11/1992 | Japan | |
| 6-80421 | 3/1994 | Japan | |
| WO94/24998 | 11/1994 | WIPO | |
| WO95/05150 | 2/1995 | WIPO | |

*Primary Examiner*—Veronica P. Hoke
*Attorney, Agent, or Firm*—Sherman and Shalloway

[57] ABSTRACT

Disclosed are ultraviolet light protective agents having the general formula:

$$(Zn_yM^{2+}_z)_{1-x}M^{3+}_xO_{1+x/2}$$

wherein $M^{2+}$ is at least one metal selected from the group consisting of Mg, Ca, Ni and Cu; and $M^{3+}$ is at least one metal selected from the group consisting of Al and Fe; as well as a sterilizer and a deodorizer which contain the compound of the above formula (I) as an effective component. They are additives to plastics, rubber, cosmetic materials, and paint and also useful as sterilizer or deodorizer, composition components.

14 Claims, No Drawings

ULTRAVIOLET PROTECTIVE AGENT

DETAILED DESCRIPTION OF THE INVENTION

1. Field of the Invention

This invention relates to an ultraviolet protective agent which comprises fine particles of a zinc compound having a specific composition and shape, and to use thereof. More specifically, it relates to an ultraviolet protective agent which has excellent ultraviolet light absorbing and screening effects and is superior in visible light transmission and stability, and to use thereof. Since the ultraviolet Protective agent of the present invention can screen harmful ultraviolet light and has transparency, it can be advantageously used as an additive to films, fibers, cosmetics and the like. Further, the zinc compound used in the present invention has excellent activities of sterilization and deodorization effect and hence, can also be used as a sterilizer or a deodorizer.

2. Prior Art

Ultraviolet light is classified into long-wavelength ultraviolet rays (UV-A), medium-wavelength ultraviolet rays (UV-B), short-wavelength ultraviolet rays (UV-C) and vacuum ultraviolet rays (vacuum UV) according to the effect of its biological action, among which ultraviolet rays having a wavelength of 297 nm or more reach the earth. Particularly harmful ultraviolet rays having a wavelength of 297 nm or less have been absorbed by the ozone layer and did not have reached the earth. However, this ozone layer has recently been destroyed by Freon or the like to form ozone holes so that the above ultraviolet rays reach the earth therethrough and certain districts become exposed to ultraviolet rays extremely harmful to living creatures. The number of cutaneous cancer patients has recently been growing worldwide, though its cause and effect are not identified. In Japan, the number of such patients has increased two times or more during the past 15 years. Ultraviolet rays which have an influence on the generation of cancer are UV-B (wavelength of 286 to 320 nm), particularly UV-B having a short wavelength of 297 nm or less. It is reported that each time the amount of ultraviolet light having such a short wavelength increases by 1%, the cancer will have a second or third power growth.

Heretofore, titanium oxide, zinc oxide, iron oxide and the like have been known as inorganic compounds for use as ultraviolet absorbing and screening agents. Since these oxides as an inorganic pigment have a high screening effect, they have a high ultraviolet screening effect. However, when they are used as a cosmetic material, they cover the skin, thereby making it difficult to retain to its niceties. Recently, ultra-fine particles of titanium oxide or zinc oxide have been used to get transparency, their surface activity is so high that they are irritative to the skin or easily agglomerate and yet they are not completely satisfactory in terms of transparency. When the above oxides are added to plastics, their transparency deteriorates in many cases. When a small amount of an oxide is added to retain the transparency of a plastic, an ultraviolet protective effect is practically lost.

To overcome these problems, JP-A-6-80421 (the term "JP-A" as used herein means an "unexamined published Japanese patent application") discloses a method of producing a scaly zinc oxide powder having an average thickness of 0.1 to 0.5 μm, an average diameter of 1 to 100 μm, an aspect ratio of 3 to 1,000 and a powder volume inherent resistivity of $10^6$ Ωcm. This prior art teaches that in this method, a scaly basic zinc salt or zinc hydroxide is deposited through a reaction between a zinc salt solution and ammonium ions. JP-B-55-25133 (the term "JP-B" as used herein means a "Japanese patent publication") discloses a method of producing a basic zinc sulfate lamellar crystal, which comprises bringing an ammonium gas into contact with an acidic aqueous solution containing zinc sulfate to absorb the ammonium gas, thereby to precipitate crystals at an acidic region. This prior art teaches that the crystal is oxidized to obtain a lamellar zinc oxide, oriented zinc oxide, lamellar zinc sulfide fluorescent material and the like as a white pigment. However, the zinc compounds proposed by these prior arts have a large particle diameter, and are not completely satisfactory because when they are used as an additive to plastics, for example, they are kneaded in fibers, thread breakage occurs or when they are blended in a film, the film has a defective outer appearance.

On the other hand, some methods of producing crystal powders containing zinc have been proposed. For example, (i) JP-B-51-37640 discloses a method of producing zinc aluminum oxide having a specific chemical composition. According to this publication, the zinc aluminum oxide has a characteristic feature that its acid strength can be changed depending on production conditions and hence, can be used for the same applications as those of regular zinc oxide, such as a catalyst, absorbent, rubber vulcanization accelerator, white pigment and the like. However, this oxide has an average secondary particle diameter of at least 10 μm, mostly at least 15 μm, and when added to a plastic, it shows a poor dispersibility and hence, it is difficult to retain transparency. (ii) JP-B-51-20997 discloses a method of producing various metal oxide particles and teaches a method of producing a zinc-containing oxide in Example 5. The particle diameter of a particle obtained in this Example 5 is large and its average secondary particle diameter is 15 μm or more. This prior art teaches that the resulting metal oxide particles can be used as a gas absorbent or gas separator to separate oxygen and nitrogen by charging it into a column and blowing air into the column, for example. Further, (iii) JP-A-48-70719 discloses a method of producing a ferrite composed of an oxide of Fe and at least one member selected from among Mg, Mn, Zn, Ni and Co and teaches that ferrite particles having an average particle diameter of 0.5 μm and composed of oxides of Ni, Zn and Fe was obtained in Example 2. Since the particles is aged under heating in an autoclave, the crystal particles do not grow well and have strong aggregation properties. Therefore, there probably exist a large number of the secondary particles having an average secondary particle diameter of 15 μm or more.

Therefore, there exist a large number of secondary particles having an average secondary particle diameter of at least 15 μm, which are produced from the particles obtained by the above methods (i) to (iii), and when they are added to plastics, transparency deteriorates and furthermore, the resulting plastics have reduced mechanical and physical properties and poor outer appearance due to inferior dispersibility.

It is therefore a first object of the invention to provide an ultraviolet protective agent which have excellent ultraviolet light absorbing and screening effects, particularly for medium-wavelength ultraviolet rays (UV-B).

It is a second object of the invention to provide an ultraviolet protective agent which is superior in visible light transmission, transparent and thermally stable.

It is a third object of the invention to provide an ultraviolet protective agent which has excellent dispersibility and can be widely used as an additive to cosmetics and plastics and further, has excellent heat resistance and durability.

Another object of the invention is to provide a shaped article which uses the above ultraviolet protective agent, and an ultraviolet protective film, in particular.

Still another object of the invention is to use the above ultraviolet protective agent for another application purpose, that is, to provide a sterilizer and a deodorizer.

According to studies conducted by the inventors of the present invention, it has been found that the above objects of the present invention can be attained by an ultraviolet protective agent which comprises fine particles of (1) a zinc compound represented by the following general formula (I):

$$(Zn_yM^{2+}_z)_{1-x}M^{3+}_xO_{1+x/2} \tag{I}$$

wherein $M^{2+}$ is at least one metal selected from the group consisting of Mg, Ca, Ni and Cu; $M^{3+}$ is at least one metal selected from the group consisting of Al and Fe; and x, y and z each satisfy $0.2 \leq x \leq 0.4$, $(y+z)=1$ and $0 \leq z \leq 0.75$.

(2) the fine particle having a major diameter of 0.1 to 2 μm, a thickness of 0.01 to 0.3 μm, an aspect ratio of 2 to 200, and an average secondary particle diameter, measured by a laser diffraction method, of not more than 5 μm.

It has been also found that other objects of the present invention can be attained by a shaped article formed of a thermoplastic resin composition containing 0.1 to 10% by weight of the above fine particles based on the total composition.

The term "ultraviolet protective agent" as used in the present invention denotes a compound having an ultraviolet light absorbing action by itself and a compound having an action to shut off the transmission of ultraviolet light when it is blended in a resin.

The ultraviolet protective agent of the present invention is described in detail hereinafter.

The fine particles for use as the ultraviolet protective agent of the present invention is a zinc compound represented by the above general formula (I) and has a specific particle shape as described above. The fine particles can be obtained by calcining a hydrotalcite compound represented by the following general formula (II) as a starting material at a temperature of 300° to 1,200° C., preferably 500° to 1,000° C.

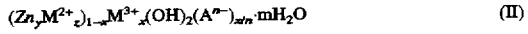

$$(Zn_yM^{2+}_z)_{1-x}M^{3+}_x(OH)_2(A^{n-})_{x/n} \cdot mH_2O \tag{II}$$

In the above formula (II), $M^{2+}$ is at least one metal selected from the group consisting of Mg, Ca, Ni and Cu, $M^{3+}$ is at least one metal selected from the group consisting of Al and Fe, $A^{n-}$ is an n-valent anion such as $CO_3^{2-}$, $OH^-$, $SO_4^{2-}$, $Cl^-$, $NO^-$, acetic acid ion, $SiO_3^{2-}$, citric acid ion, ferrocyane ion and the like, among which $CO_3^{2-}$ is preferred.

M is a positive number of 1 to 10, for example, and x, y and z each satisfy $0.2 \leq x \leq 0.4$, $(y+z)=1$ and $0 \leq z \leq 0.75$.

The hydrotalcite compound represented by the above general formula (II) is a solid solution of various metal hydroxides having a rhombohedral structure and a hexagonal lamellar crystal. Therefore, since zinc (Zn) and other metal form the solid solution in the present invention, it is considered but not identified that the impediment of the crystal growth of ZnO leads to reduced density and refractive index and improved transparency.

As the method of producing the hydrotalcite compound as a starting material for advantageously obtaining the ultraviolet protective agent of the present invention which is superior in visible light transmission, known methods as disclosed in JP-B-46-2280, JP-B-47-32198, JP-B48-29477 and JP-B-51-29129 may be employed except that a predetermined amount of a water-soluble Zn salt must be necessarily contained in the starting material. For instance, an acidic solution mixture of 0.53 mol of zinc nitrate $Zn(NO_3)_2 \cdot 6H_2O$, 0.17 mol of magnesium nitrate $Mg(NO_3)_2 \cdot 6H_2O$ and 0.03 mol of aluminum nitrate $Al(NO_3)_3 \cdot 9H_2O$ dissolved in 1,000 ml of purified water and an alkaline solution mixture of 0.15 mol of sodium carbonate $Na_2CO_3$ and 2.0 mols of sodium hydroxide NaOH dissolved in 1,000 ml of purified water are simultaneously poured into a reactor containing water in such an amount that it can be stirred, under stirring. The amount of the alkaline solution mixture is so controlled to maintain pH at 9.0 to 10.5 (which differs according to element and is not limited). The reaction temperature may be on the order of room temperature to 50° C. The resulting precipitate is filtered under reduced pressure and washed with water, and then is aged, while heating, in an autoclave at 120° C. for 10 hours. The thus obtained product is dehydrated, dried at 80° C. for 12 hours, ground with a hammer mill, and calcined at 300° to 1,200° C. to obtain the zinc compound of the present invention.

Preferably, the hydrotalcite compound suitable to obtain the fine particles of the present invention has an average major diameter, measured through a scanning electron microscope, of 0.1 to 2 μm, an average thickness of 0.01 to 0.3 μm, an average secondary particle diameter, measured by a laser diffraction method (Microtrack method), of not more than 5 μm and a maximum particle diameter of not more than 15 μm. The fine particles can be advantageously obtained by heating the hydrotalcite compound of the general formula (II) obtained by the above methods, for example, in an autoclave and in a water medium at a temperature of about 80° to 170° C., preferably about 100° to 150° C., for about 5 to 40 hours. The heat treatment conditions are not limited, but the above conditions are recommended to obtain the desired particle shape. When the content of Zn is large, zinc oxide is liable to form in the heating treatment. Therefore, heating may be carried out under the above conditions so as not to generate zinc oxide and to satisfy the above average major diameter, average thickness and average secondary particle diameter.

The thus obtained hydrotalcite compound itself has an ultraviolet screening effect to some degree, but its effect is not satisfactory. Therefore, the above hydrotalcite compound is calcined in an oxidizing or inert gas atmosphere under an increased, normal or reduced pressure at 300° to 1,200° C., preferably 500° to 1,000° C. to obtain a compound represented by the above general formula (I) in the form of a fine particle which can absorb and screen ultraviolet light more effectively. For example, any furnace may be used, provided that calcining can be performed at 300° to 1,200° C. for 10 minutes to 4 hours, and may be exemplified by a ring furnace, box furnace, kiln furnace, gas furnace and the like. To further enhance calcining efficiency, the hydrotalcite compound may be granulated to an appropriate size and calcined. The calcined product may be ground to a desired particle size and classified according to application purpose.

As for the zinc compound of the present invention, in the above general formula (I), $M^{2+}$ is at least one metal selected from the group consisting of Mg, Ca, Ni and Cu, among which $Mg^+$ is preferred. $M^{3+}$ is Al, Fe or a combination of both, among which Al is preferred. In the general formula (I), x, y and z each satisfy $0.2 \leq x \leq 0.4$, $(y+z)=1$ and $0 \leq z \leq 0.75$. The particle of the compound represented by the above general formula (I) has a lamellar crystal form with a major diameter of 0.1 to 2 µm and a thickness of 0.01 to 0.3 µm and a particle form with an aspect ratio (major diameter/thickness) of 2 to 200. Further, the compound preferably has an average secondary particle diameter, measured by a laser diffraction method (Microtrack method), of not more than 5 µm, more preferably no more than 4 µm, and a maximum particle diameter of no more than 15 µm, more preferably no more than 10 µm. The lower limit of the average secondary particle diameter is generally 0.2 µm.

The compound of the present invention represented by the above general formula (I) is a solid solution and a particle having a lamellar crystal form, and has transparency and excellent effects of absorbing and screening ultraviolet rays, particularly medium-wavelength ultraviolet rays (UV-B). Therefore, the particles can be used as an ultraviolet absorbent or an ultraviolet screening agent in a wide range of fields.

When the ultraviolet protective agent of the present invention is blended in a shaped article of a resin such as a film, sheet, fiber or the like, it can suppress the deterioration of the resin by ultraviolet light. An object of the resin used includes resins which deteriorate by ultraviolet light, and another object of the resins includes resins which are transparent and can shut off the transmission of ultraviolet light when they are blended with the ultraviolet protective agent of the present invention. The resin may be crystalline or non-crystalline, or transparent, translucent or non-transparent. Further, the shaped article may be in the form of a film, sheet, fiber or the like.

However, the ultraviolet protective agent of the present invention has high transparency and a satisfactory ultraviolet screening effect even if it is contained in a small amount, as described above. Therefore, when it is blended into a thermoplastic resin having high transparency, shaped articles, especially films and sheets, having an excellent ultraviolet screening effect while retaining transparency can be obtained. Such transparent films and sheets are used as ultraviolet protective materials for packages and containers and are of great value.

The thermoplastic resin from which a transparent film or sheet can be formed may be polyolefins such as polyethylene, polypropylene and polybutene; polyesters such as polyethylene terephthalate, polybutylene terephthalate and polyethylene-2,6-naphthalate; polycarbonates; polyamides such as nylon 6, nylon 6,6, and nylon 6,10; poly(meth)acrylates such as polymethacrylate and polymethyl methacrylate; polyvinyl chloride; vinyl chloride-vinyl acetate copolymers; and the like.

A film formed of the above transparent thermoplastic resin alone (i.e., containing the ultraviolet protective agent) has a total visible light transmittance of at least 90%, preferably at least 95%. This total visible light transmittance is a value measured for a 100 µm thick film.

A film having an excellent ultraviolet screening effect while retaining transparency can be obtained by blending the ultraviolet protective agent of the present invention into the thermoplastic resin in an amount of 0.1 to 10% by weight, preferably 0.2 to 5% by weight. Particularly, an ultraviolet protective film having an ultraviolet screening rate of at least 50%, preferably at least 60% can be obtained. This film has high transparency with a total visible light transmittance of at least 70%, preferably at least 80%.

Thermoplastic resin containing the ultraviolet protective agent of the present invention may further contain a known ultraviolet absorbent.

Further, the thermoplastic resin containing the ultraviolet protective agent of the present invention may be in the form of a fiber in addition to the above film (or sheet). When it is a fiber, it makes it possible not only to prevent deterioration by ultraviolet light but also to suppress the influence of ultraviolet light on the skin when one wears clothes formed of the fiber.

The ultraviolet protective agent of the present invention can be used in other fields, making use of its ultraviolet absorbing and screening effects as well as its transparency and fine particle shape. For example, it is advantageously used as an effective component of a coating composition for protecting the skin from ultraviolet light. In this way, according to the present invention, there is provided a coating composition for protecting the skin from harmful ultraviolet light. This composition may be exemplified by cosmetic compositions such as a milky lotion and cream, skin oil, skin powder and the like. The ultraviolet protective agent is generally contained in these coating compositions in an amount of 1 to 10% by weight.

The composition for protecting the human skin, when it covers the skin, has excellent transparency and an outstanding ultraviolet screening effect because the ultraviolet protective agent is fine particles of a lamellar crystal and superior in visible light transmission.

Since the ultraviolet protective agent of the present invention is also excellent in dispersibility and durability, it is effective in preventing deterioration by ultraviolet light when it is blended in paint or ink.

The ultraviolet protective agent and composition of the present invention may be used as a filler or stabilizer for resins or rubber to further improve compatibility and dispersibility, and may be used together with a surface modifier or other additive with a view to further improve touch and spreadability for application in paint, cosmetics and the like.

Illustrative examples of the surface modifier include higher fatty acids, metal soap, silicone oil, hydrocarbon oil, anionic surfactants, silane coupling agents, titanate coupling agents, aluminum coupling agents, glycerin, fatty acid esters, waxes such as fish wax and Japan wax and the like.

Surface treatment may be carried out in a gas phase, in a liquid layer or in vacuum by any conventional methods.

According to studies conducted by the inventors, it has been found that the zinc compound represented by the above general formula (I) has sterilizing and deodorizing effects in addition to the above effects as an ultraviolet protection agent. According to the present invention, therefore, there is provided a sterilizer and a deodorizer containing the zinc compound of the above general formula (I) as an effective component. As the sterilizer and deodorizer, the compound can be used directly or upon having been blended into other liquid carrier or solid carrier. To enhance an antifungal effect, for example, the above zinc compound may be used in combination of a commercially available antifungus agent. Among commercially available antifungus agents, a silver-based antifungus agent is superior in heat resistance and persistent efficacy. However, the silver-based antifungus agent itself or its resin composition is unstable against light exposure and hence, discolors at the time of use or processing with the result of poor outer appearance. Therefore, the zinc compound of the present invention is effective in preventing such discoloration. The content of the compound is usually 5 to 90% by weight, preferably 10 to 80% by weight. Examples of the liquid carrier include water, alcohols, ethers, ketones, hydrocarbons and the like, and examples of the solid carrier include kaolin, talc, diatomaceous earth, high molecular weight compounds and the like.

Examples

The following examples are provided for the purpose of further illustrating the present invention but are in no way to be taken as limiting. Average major diameter and average thickness were measured through an electron microscope, and average secondary particle diameter was measured by a laser diffraction method (Microtrack method). This laser diffraction method was carried out by controlling the content of sample particles in a 0.2% aqueous solution of hexametaphosphoric acid to 1% and subjecting the solution to an ultrasonic dispersion treatment.

Example 1

(1) preparation of hydrotalcite compound

A hydrotalcite compound was prepared by a known method. That is, an acidic solution of 0.7 mol of zinc chloride $ZnCl_2$ and 0.15 mol of aluminum sulfate $Al_2(SO_4)_2$ dissolved in 1,000 ml of purified water and an alkaline solution of 0.15 mol of sodium carbonate $Na_2CO_3$ and 2.0 mols of sodium hydroxide NaOH dissolved in 1,000 ml of purified water were poured simultaneously into a reactor adjusted to 30° C. and containing water in such an amount that it can be stirred, under stirring, to maintain pH at 9.5. The resulting precipitate of a hydrotalcite compound, $Zn_{0.7}Al_{0.3}(OH)_2(CO_3)_{0.15} \cdot 0.5H_2O$, was filtered under reduced pressure and washed with water.

(2) preparation of zinc compound

The above hydrotalcite compound was aged under heating in water at 90° C. for 15 hours, dried, ground with a hammer mill, and calcined in a box furnace in an aerial atmosphere at 500° C. for 1 hour. The thus obtained oxide represented by $Zn_{0.7}Al_{0.3}O_{1.15}$ had an average major diameter of 0.6 μm and an average thickness of 0.1 μm (aspect ratio: 6). Its average secondary particle diameter was 0.9 μm and maximum particle diameter was 3.1 μm.

(3) preparation of resin composition

Using the above zinc compound, a polypropylene resin comprising the following components (i) to (iv) was formed into a 100 μm thick film, and the film was measured for its visible light transmission and haze with a haze meter of Tokyo Denshoku Technical Center Co., Ltd. and for its ultraviolet absorbing power with a spectrophotometer (Model 150-20-type Double Beam of Hitachi Ltd., with an integrating sphere) and ultraviolet screening rate with a spectrophotometer (Model 150-20-type Double Beam of Hitachi Ltd., without integrating sphere). The results are shown in Table 1.

| (i) | polypropylene | 100 parts by weight |
| (ii) | oxide of the above composition | 1 part by weight |
| (iii) | phenolic antioxidant | 0.05 part by weight |
| (iv) | organic phosphoric antioxidant | 0.05 part by weight |

Pentaerythrityl-tetrakis[3-(3,5-di-t-butyl-4-hydroxyphenylpropionate)] (Irganox 1010 of Chiba Geigy Co.) was used as the phenolic antioxidant (iii) and cyclic neopentane tetraylbis(2,4-di-t-butylphenyl)phosphite (URTRANOX 626 of GE Corporation) was used as the organic phosphoric antioxidant (iv).

Example 2

A hydrotalcite compound represented by $(Zn_{0.3}Mg_{0.7})_{0.8}Al_{0.2}(OH)_2(CO_3)_{0.1} \cdot 0.7H_2O$ was aged under heating in water at 150° C. for 8 hours, dried, ground and calcined at 900° C. for 1 hour to produce an oxide represented by $(Zn_{0.3}Mg_{0.7})_{0.8}Al_{0.2}O_{1.1}$ having an average major diameter of 1.2 μm, an average thickness of 0.2 μm (aspect ratio: 6), an average secondary particle diameter of 1.6 μm and a maximum particle diameter of 4.4 μm. The oxide was measured for particle size through an electron microscope as in Example 1 and evaluated. The results are shown in Table 1.

Example 3

A hydrotalcite compound represented by $(Zn_{0.5}Mg_{0.5})_{0.7}Al_{0.15}Fe_{0.15}(OH)_2(CO_3)_{0.15} \cdot 0.5H_2O$ was aged under heating in water at 120° C. for 15 hours, dried, ground and calcined at 500° C. to produce an oxide represented by $(Zn_{0.5}Mg_{0.5})_{0.7}Al_{0.15}Fe_{0.15}O_{1.15}$ having an average major diameter of 0.4 μm, an average thickness of 0.05 μm (aspect ratio: 8), an average secondary particle diameter of 3 μm and a maximum particle diameter of 12.6 μm. The oxide was evaluated in the same manner as in Example 1. The results are shown in Table 1.

Example 4

A hydrotalcite compound represented by $Zn_{0.7}Fe_{0.3}(OH)_2(CO_3)_{0.15} \cdot 0.5H_2O$ was aged under heating in water at 120° C. for 8 hours, dried, ground and calcined at 600° C. to produce an oxide represented by $Zn_{0.7}Fe_{0.3}O_{1.15}$ having an average major diameter of 0.6 μm, an average thickness of 0.2 μm (aspect ratio: 3), an average secondary particle diameter of 0.8 μm and a maximum particle diameter of 12.6 μm. The oxide was treated with 5% of stearic acid at 80° C. using a Henschel mixer. The thus obtained oxide was evaluated in the same manner as in Example 1. The results are shown in Table 1.

Example 5

A hydrotalcite compound represented by $(Zn_{0.87}Ni_{0.13})_{0.67}Al_{0.33}(OH)_2(CO_3)_{0.17} \cdot 0.5H_2O$ and obtained by a known method was aged under heating in water at 120° C. for 15 hours, dried, ground with a hammer mill and calcined in a box furnace in an aerial atmosphere at 500° C. for 1 hour. The thus obtained oxide represented by $(Zn_{0.87}Ni_{0.13})_{0.67}Al_{0.33}O_{1.17}$ had an average major diameter of 0.3 μm, an average thickness of 0.02 μm (aspect ratio: 15), an average secondary particle diameter of 4.0 μm and a maximum particle diameter of 8.9 μm. The thus obtained oxide was evaluated in the same manner as in Example 1. The results are shown in Table 1.

Example 6

A hydrotalcite compound represented by $(Zn_{0.87}Ca_{0.13})_{0.67}Al_{0.33}(OH)_2(NO_3)_{0.33} \cdot 0.5H_2O$ and obtained by a known method was aged under heating in water at 100° C. for 15 hours, dried, ground with a hammer mill and calcined in a box furnace in an aerial atmosphere at 500° C. for 1 hour. The thus obtained oxide represented by $(Zn_{0.87}Ca_{0.13})_{0.67}Al_{0.33}O_{1.17}$ had an average major diameter of 0.6 μm, an average thickness of 0.05 μm (aspect ratio: 12) and an average secondary particle diameter of 5.0 μm. The thus obtained oxide was evaluated in the same manner as in Example 1. The results are shown in Table 1.

Comparative Example 1

One part by weight of commercially available zinc oxide having an average particle size, measured by a Microtrack method, of 1.3 μm was kneaded into 100 parts by weight of a polypropylene film in the same manner as in Example 1, and the resulting product was evaluated in the same manner as in Example 1. The results are shown in Table 1.

Comparative Example 2

0.4 part by weight of commercially available zinc oxide was kneaded into a polypropylene film in the same manner as in Comparative Examples 1, and the resulting product was evaluated in the same manner. The results are shown in Table 1.

Comparative Example 3

The hydrotalcite obtained in Example 1 and prior to aging under heating at 90° C. was dried, ground with a hammer mill and then calcined in the same manner as in Example 1 to produce an oxide. The thus obtained oxide had mostly a major diameter of not more than 0.1 μm and was thin with an average secondary particle diameter of 7.8 μm and a maximum particle diameter of 25.1 μm or more. When this oxide was evaluated In the same manner as in Example 1, it was found that the resulting film had a number of white grains. Therefore, the film was of little commercial value. The results are shown in Table 1.

Comparative Example 4

A polypropylene resin film was obtained as in the same manner as in Example 1 except that no oxide was added. The results are shown in Table 1.

TABLE 1

| Example No. | Total visible light transmittance (%) | Haze | Ultraviolet absorbing power 286 nm | Ultraviolet screening rate 286 nm (%) |
|---|---|---|---|---|
| Example 1 | 88.6 | 30.6 | 0.75 | 89 |
| Example 2 | 88.3 | 33.5 | 0.56 | 82 |
| Example 3 | 86.9 | 36.1 | 0.77 | 90 |
| Example 4 | 85.5 | 33.2 | 0.80 | 93 |
| Example 5 | 87.2 | 31.5 | 0.75 | 88 |
| Example 6 | 87.5 | 37.2 | 0.71 | 85 |
| Comparative Example 1 | 84.8 | 55.6 | 0.76 | 84 |
| Comparative Example 2 | 85.7 | 34.4 | 0.52 | 50 |
| Comparative Example 3 | 88.0 | 28.9 | 0.50 | 50 |
| Comparative Example 4 | 88.7 | 18.3 | 0.40 | 28 |

Example 7

One part by weight of the zinc compound obtained in Example 1 and represented by $Zn_{0.7}Al_{0.3}O_{1.15}$ was added to 100 parts by weight of each of the commercial resins shown in Table 2 below, and thoroughly mixed to prepare an uniform mixture. Pellets of a resin composition were prepared from this mixture with a kneading extruder and extruded into a 100 μm thick film with a film molding extruder. The properties of the thus obtained film were evaluated in the same manner as in Example 1. A film which did not contain the zinc compound was also evaluated. The results are shown in Table 2.

TABLE 2

| Type of films* | Total visible light transmittance (%) | Ultraviolet absorbing power 286 nm | Ultraviolet screening rate 286 nm (%) |
|---|---|---|---|
| soft polyvinyl chloride resin (yes) | 87.5 | 2.1 | 100 |
| soft poly- | 89.4 | 1.5 | 100 |
| vinyl chloride resin (no) | | | |
| polycarbonate resin (yes) | 88.9 | 1.3 | 99 |
| polycarbonate resin (no) | 93.4 | 0.7 | 90 |
| methacrylic resin (yes) | 88.6 | 1.2 | 90 |
| methacrylic resin (no) | 93.8 | 0.3 | 31 |

Example 8

A hydrotalcite represented by $Zn_{0.7}Al_{0.3}(OH)_2(CO_3)_{0.15} \cdot 0.5H_2O$ was aged under heating in water at 120° C. for 6 hours, dried, ground with a hammer mill and calcined in a box furnace in an aerial atmosphere at 500° C. for 1 hour to produce $Zn_{0.7}Al_{0.3}O_{1.15}$. The thus obtained oxide had an average major diameter of 0.6 μm, an average thickness of 0.1 μm and an average secondary particle diameter of 0.9 μm. The thus obtained product was kneaded at 230° C. to prepare the following resin composition, and the composition was press-molded at 190° C. for 10 minutes to form a No.2 dumbbell based on JIS K 7113 which then was subjected to an accelerated weathering test with a sunshine weather meter.

TABLE 3

(Compounding and result)

| | | | | | |
|---|---|---|---|---|---|
| LDPE | 100 phr | 100 phr | 100 phr | 100 phr | 100 phr |
| TINUVIN 622LD | 0.1 phr | 0.2 phr | 0.3 phr | 0.3 phr | 0.3 phr |
| Oxide | 0.5 phr | 0.5 phr | 0.5 phr | | |
| Uncalcined product | | | | | 0.5 phr |
| Before exposure | | | | | |
| Strength at break (Kgf/mm²) | 1.72 | 1.62 | 1.63 | 1.60 | 1.66 |
| Elongation % | 590 | 620 | 600 | 620 | 590 |
| After 600 hrs exposure* | | | | | |
| Retention of strength at break (%) | 80 | 81 | 95 | 77 | 72 |
| Retention of elongation (%) | 91 | 85 | 91 | 79 | 75 |

(Note)
LDPE: low-density polyethylene (LF440B, a product of Dia Polymer Co. Ltd)
TINUVIN 622LD: polycondensate of succinic acid and dimethyl-1-(2-hydroxyethyl)-4-hydroxy-2,2,6,6-tetramethylpiperidine
*Accelerated exposure test equivalent to 600 hours exposure to sunshine

Example 9

The following blend composition was mixed to form pellets with a single-screw extruder at 200° C. The pellets were press-molded at 190° C. for 10 minutes to form 20×40 mm test pieces having a thickness of 1 mm, and the test pieces was subjected to outdoor exposure tests for 1 week and 1 month. The test pieces were measured for their yellowness index YI with a color difference meter. A commercially available antifungus agent (Bactenon AZ of Gel Technology Co.) was used as a silver-based antifungus agent. A zinc compound represented by $(Zn_{0.3}Mg_{0.7})_{0.67}Al_{0.33}O_{1.15}$ having an average major diameter of 0.5 μm, an average thickness of 0.1 μm (aspect ratio: 5) and an average secondary particle diameter of 0.8 μm which was obtained by aging, while heating, a hydrotalcite represented by $(Zn_{0.3}Mg_{0.7})_{0.67}Al_{0.33}(OH)_2(CO)_{0.16} \cdot 0.5H_2O$ in water at 150° C. for 6 hours, drying, grinding and calcining at 500° C. for 1 hour was used. For comparison, an uncalcined product was also evaluated. The results are shown in Table 4.

| Compounding composition | |
|---|---|
| Low-density polyethylene | 100 parts by weight |
| Antifungus agent (Bactenon AZ) | 1 part by weight |
| Antioxidant (Irganox 1010) | 0.1 part by weight |
| Zinc compound | 1 part by weight |

TABLE 4

| | Results of outdoor weather test | | |
|---|---|---|---|
| Zinc compound | Right after molding | After 1 week (YI) | After 1 month (YI) |
| Calcined product | 7.5 | 7.8 | 7.5 |
| Uncalcined product | 18.9 | 27.6 | 23.6 |
| product not added | 11.8 | 52.7 | 41.8 |

Example 10

10 g of $Zn_{0.7}Al_{0.3}O_{1.15}$ obtained in Example 1 was added to 1.0 kg of commercially available polyethylene pellets (LF 440B of Dia Polymer Co.) and mixed in a polyethylene bag to obtain an uniform mixture which was then formed into a 50 μm thick film with a kneading extruder at 200° C. and subjected to an anti-fungus test. In the test, 0.75 g of the 10 mm square film was sampled by a shake-flask incubation method, and treated with a test solution having a concentration of $9.9 \times 10_5$ coli bacilli/ml at 25° C. for 24 hours.

When the fungi-concentration of the test solution after the treatment was measured, the fungus reduction rate was found to be 98%.

Since the fungus reduction rate in a blank test was not more than 10% and that of a 50 μm thick film formed of the same polyethylene pellet only in a blank test was no more than 30%, the oxide was recognized to have effective antifungal properties.

Example 11

A hydrotalcite compound represented by $(Zn_{0.75}Cu_{0.25})_{0.7}Al_{0.3}(OH)_2(CO_3)_{0.15} \cdot 0.5H_2O$ was aged under heating in water at 110° C for 15 hours, dehydrated, dried and granulated. The resulting product was calcined at 800° C. for 1 hour and ground with a test ball mill for 6 hours to produce an oxide of $(Zn_{0.75}Cu_{0.25})_{0.7}Al_{0.3}O_{1.15}$ having an average major diameter of 0.3 μm, an average thickness of 0.05 μm (aspect ratio: 6), an average secondary particle diameter of 4.3 μm and a maximum particle diameter of 4.4 μm. The fungus reduction rate of this sample was measured in the same manner as in Example 11 and found to be 99%.

Example 12

A worn-out floorcloth was cut into two pieces, one piece was immersed in a 5% aqueous suspension of the oxide of Example 11 and the other piece was immersed in city water. Both pieces were taken out, squeezed slightly and left in a desiccator filled with a slight amount of water at 30° C. for 48 hours. When they were examined with the human olfactory sense, it was found that the piece immersed in the oxide didn't smell whereas the piece immersed in city water smelt offensive.

Example 13

All of the amounts of the following powdery cosmetic materials excluding perfume were charged into a small-size mill (a product of Kyoritsu Riko Co.) and mixed for 5 minutes, and thereafter, perfume was added to the resulting mixture and mixed for 1 minute.

| talc | 50% |
|---|---|
| cellulose | 30% |
| zinc compound (obtained in Example 1) | 10% |
| synthetic silica | 9.95% |
| perfume | 0.05% |

The thus obtained sample was adhered to adhesive cellophane tape and set in the sample side of a spectrophotometer. Adhesive cellophane tape of the same type was set in the reference side of the meter to measure the screening rate of ultraviolet light having a wavelength of 286 nm. It was found to be 98.0%. The amount of the powdery cosmetic product adhered to the cellophane tape was 0.80 mg/cm².

Subsequently, the powdery cosmetic product having the above composition was press-molded into a 2 cm tablet which was measured for its ultraviolet absorbing power at a wavelength of 286 nm with a spectrophotometer with an integrating sphere and found to be 0.56.

Comparative Example 5

A powdery cosmetic product was obtained in the same manner as in Example 13 except the same amount of calcium carbonate having an average particle diameter of 1 μm was used in place of the oxide and measured for its ultraviolet screening rate.

The screening rate of ultraviolet light having a wavelength of 286 nm was 96.1%. The amount of the powder cosmetic product adhered to cellophane tape was 0.81 mg/cm².

Subsequently, the powdery cosmetic product was press molded into a 2 cm tablet which was measured for its ultraviolet absorbing power at a wavelength of 286 nm with a spectrophotometer with an integrating sphere and found to be 0.07. Therefore, it was verified to have no ultraviolet absorbing power.

What is claimed is:

1. An ultraviolet protective agent which comprises fine particles of
(1) a zinc compound represented by the following general formula (I):

$$(Zn_yM^{2+}_z)_{1-x}M^{3+}_xO_{1+x/2} \qquad (I)$$

wherein $M^{2+}$ is at least one metal selected from the group consisting of Mg, Ca, Ni and Cu; $M^{3+}$ is at least one metal selected from the group consisting of Al and Fe; and x, y and z each satisfy $0.2 \leq x \leq 0.4$, $(y+z)=1$ and $0 \leq z \leq 0.75$.

(2) the fine particle having a major diameter of 0.1 to 2 μm, a thickness of 0.01 to 0.3 μm, an aspect ratio of 2 to 200, and an average secondary particle diameter, measured by a laser diffraction method, of not more than 5 μm.

2. The ultraviolet protective agent of claim 1, wherein $M^{2+}$ in the general formula (I) is Mg.

3. The ultraviolet protective agent of claim 1, wherein $M^{3+}$ in the general formula (I) is Al.

4. The ultraviolet protective agent of claim 1, wherein the fine particle has a major diameter of 0.2 to 2 μm, a thickness of 0.02 to 0.2 μm, an aspect ratio of 3 to 100 and an average secondary particle diameter, measured by a laser diffraction method, of not more than 4 μm.

5. A shaped article formed of a thermoplastic resin composition containing 0.1 to 10% by weight of the fine particle described in claim 1, based on the total composition.

6. The shaped article of claim 5 which has an ultraviolet screening rate of at least 50%.

7. The shaped article of claim 5 which has a total visible light transmittance of at least 80%.

8. The shaped article of claim 5, to which the thermoplastic resin provides a total visible light transmittance of at least 95%.

9. The shaped article of claim 5, wherein the thermoplastic resin is selected from the group consisting of polyolefins, polyesters, polycarbonates, polyamides, poly(meth)acrylates, polyvinyl chloride and vinyl chloride-vinyl acetate copolymers.

10. The shaped article of claim 5, which is a film.

11. The shaped article of claim 5, which is used as an ultraviolet protective film.

12. The shaped article of claim 5, which is a fiber.

13. A sterilizer which contains the fine particle described in claim 1 as an effective component.

14. A deodorizer which contains the fine particle described in claim 1 as an effective component.

* * * * *